United States Patent [19]
Takei et al.

[11] Patent Number: 5,980,574
[45] Date of Patent: Nov. 9, 1999

[54] ARTIFICIAL SOCKET, SCREW FOR FIXING ARTIFICIAL SOCKET AND ARTIFICIAL HIP JOINT

[75] Inventors: Tunenori Takei, 5-7, Tokuma 1-chome; Hajime Yamada, 668-10, Aokishima-otsu, Aokishima-cho, both of Nagano-shi, Nagano-ken; Satoshi Ojima; Masanori Nakasu, both of Tokyo, all of Japan

[73] Assignees: Asahi Kogaku Kogyo Kabushiki Kaisha, Tokyo; Tunenori Takei; Hajime Yamada, both of Nagano-ken, all of Japan

[21] Appl. No.: 09/000,946

[22] Filed: Dec. 30, 1997

[30] Foreign Application Priority Data

Jan. 6, 1997 [JP] Japan .................................. 9-000415

[51] Int. Cl.$^6$ .................................. A61F 2/34; A61F 2/28
[52] U.S. Cl. .................................. 623/22; 623/19; 623/16
[58] Field of Search .................................. 623/16, 22, 23, 623/19

[56] References Cited

U.S. PATENT DOCUMENTS

| | | |
|---|---|---|
| 4,113,500 | 9/1978 | Ebihara et al. . |
| 4,781,183 | 11/1988 | Casey et al. . |
| 4,839,215 | 6/1989 | Starling et al. . |
| 4,842,604 | 6/1989 | Dorman et al. ............................ 623/16 |
| 4,904,257 | 2/1990 | Mori et al. . |
| 4,919,751 | 4/1990 | Sumita et al. . |
| 4,969,913 | 11/1990 | Ojima . |
| 5,082,803 | 1/1992 | Sumita . |
| 5,180,426 | 1/1993 | Sumita . |
| 5,281,404 | 1/1994 | Sumita . |

FOREIGN PATENT DOCUMENTS

| | | | |
|---|---|---|---|
| 2 664 501 A1 | 1/1992 | France ..................................... 623/16 |
| 40 02 841 A1 | 7/1990 | Germany ................................. 623/16 |

Primary Examiner—David H. Willse
Attorney, Agent, or Firm—Greenblum & Bernstein, P.L.C.

[57] ABSTRACT

An artificial socket comprising a composite body of a calcium phosphate compound and an in vivo-absorptive polymeric material. The artificial socket is embedded and secured in the pelvis side of the artificial hip joint. The socket has a configuration of a semi-spherical shell body, and the thickness thereof is thinner than that of a conventional artificial socket and the inner diameter thereof is substantially the same as that of a real socket in a human bone. An artificial hip joint using the artificial socket and a fixing screw suitable for the fixation of the socket in the pelvis are also disclosed.

25 Claims, 5 Drawing Sheets

Fig. 5
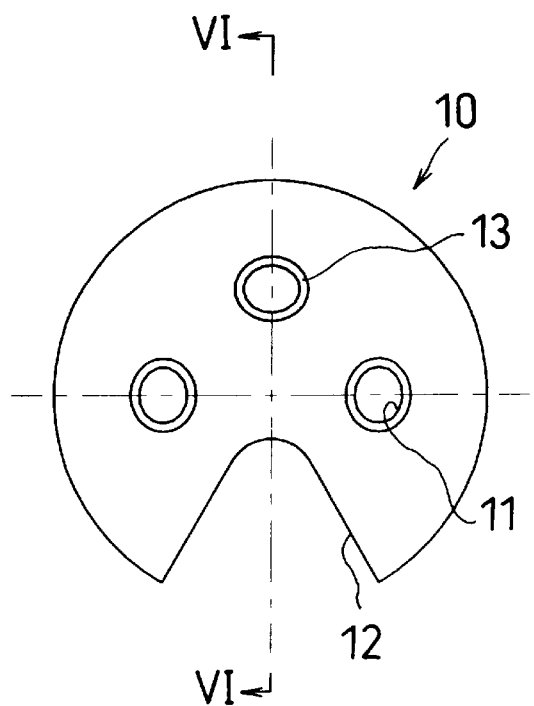
Fig. 6
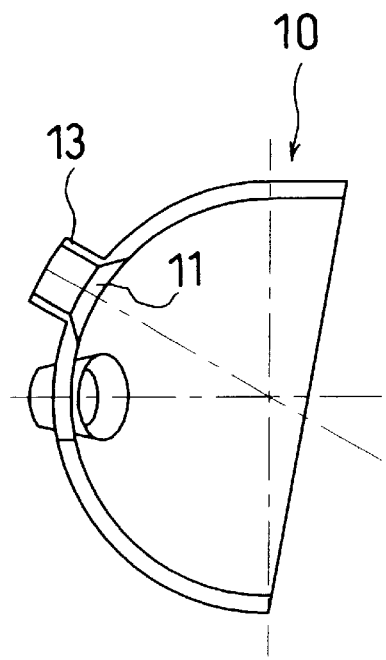
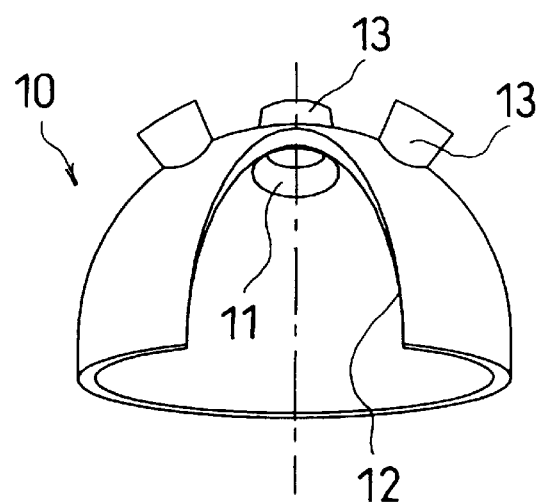
Fig. 7

Fig. 8
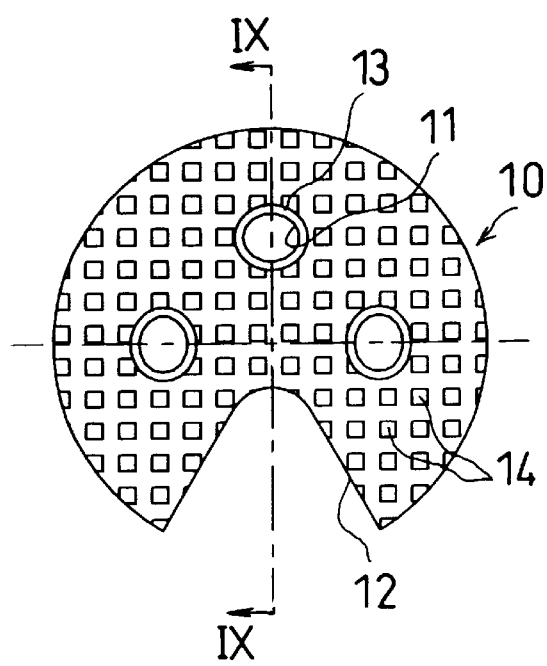
Fig. 9
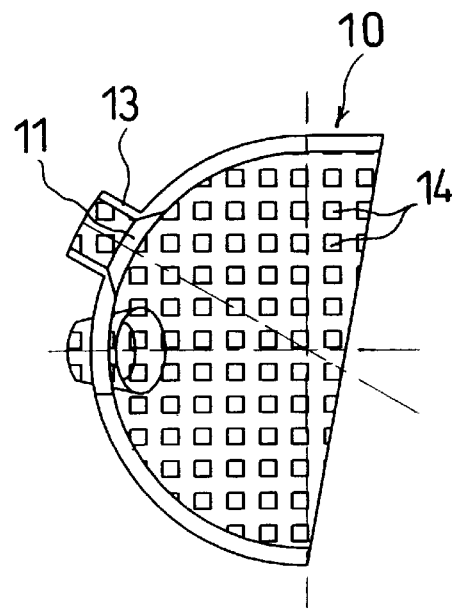
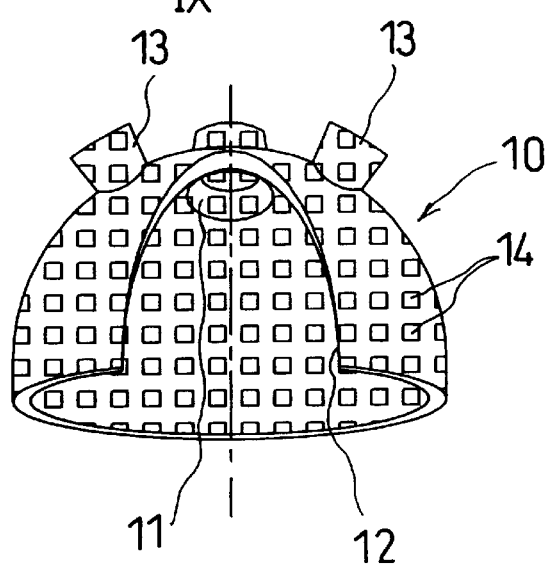
Fig. 10

ARTIFICIAL SOCKET, SCREW FOR FIXING ARTIFICIAL SOCKET AND ARTIFICIAL HIP JOINT

BACKGROUND OF THE INVENTION

1. Field of the Invention

The present invention relates to an artificial socket for use in an artificial hip joint, a fixing screw for securing the artificial socket in an artificial hip joint, and an artificial hip joint using the artificial socket.

2. Description of the Related Art

An artificial hip joint comprises an artificial socket to be embedded and secured in a pelvis, and a stem which is embedded and secured in an upper end of the femur and a tip portion of which stem is provided with an artificial caput capable of being freely rotatably fitted in the artificial socket. Hitherto, a variety of artificial sockets and artificial hip joints, typical examples of which will be described below, have been utilized in the field of orthopedic surgery:

1) a cement bonding-type total artificial hip joint in which a socket and a stem are formed from a plastic material such as polyethylene and a metal material, respectively, and they are bonded with a cementing material such as bone cement, and a cementless bonding-type total artificial hip joint in which no cementing material such as bone cement is used in the bonding of a socket to a stem;

2) a metal-on-metal type total artificial hip joint in which a socket and a caput (bone head) both are formed from a metal material, the socket as a metal cap is supported by a plastic material such as polyethylene, and they are fixed to a human bone with a cementing material such as bone cement; and 3) a ceramic-to-ceramic type total artificial hip joint in which a socket and a caput both are formed from a hard ceramic material, and they are fixed to a human bone with a cementing material such as bone cement.

However, these conventional artificial hip joints have the following problems to be solved.

The cement bonding-type total artificial hip joint has been developed to solve the problems in the artificial caput integrally formed from the caput and stem, both being of a metal material, and thus a socket thereof is also made of an artificial material. As mentioned above, in this type of the artificial hip joint, the socket is formed from polyethylene, the stem is formed from the metal material, and the socket and the stem are secured via the bone cement on the pelvis as a mother base. Since the caput has a small diameter such as about 22 mm and such small diameter limits a movable range of the socket and the caput due to the narrowed latitude of the conformability of the socket with the caput, there is a possibility that a subluxation is caused in the artificial hip joint. Further, there are drawbacks that the deformation of the polyethylene used in the socket can cause loosening and wearing of the hip joint, and that only a low bonding strength can be obtained between the bone cement and the mother base. Furthermore, with regard to use of the artificial hip joint for an extended period of time, there has been made a report that wearing of polyethylene can cause loosening of the joint, because fine powders of the worn polyethylene are distributed around the stem embedded in the femur.

Similar problems are caused in the cementless bonding-type total artificial hip joint using no bonding cement, because the socket of the hip joint is made from polyethylene as in the above-mentioned cement bonding-type artificial hip joint. For this type of the artificial hip joint, deterioration of polyethylene due to its in vivo oxidation can not be avoided. Moreover, there has not been any suggested countermeasure against such wearing of the socket which is caused as a result of the deterioration of polyethylene.

The metal-on-metal type total artificial hip joint has been developed to prevent drawbacks such as reduction of lubricating properties and wearing of polyethylene which are caused due to deformation and oxidative deterioration of polyethylene. For such an artificial hip joint, however, since the socket of the metal material is supported by polyethylene and the joint is bonded through the bone cement to the living body (i.e., the pelvis), it is unable to avoid deterioration of polyethylene due to its in vivo oxidation, and thus the hip joint can not ensure sufficient wear prevention.

The ceramic-to-ceramic type total artificial hip joint is an artificial hip joint in which both of the socket and the caput are formed from hard ceramic material, such as alumina and zirconia. For such a hip joint, since the hard ceramic socket has only an instable strength, it is necessary to largely increase the thickness of the socket in the production of the hip joint. As an essential result, the diameter of the caput used in combination with the socket must be reduced so that it can conform with the configuration of the socket. Further, this hip joint suffers from drawbacks such as a reduced shock-absorbing property than that of the polyethylene-made hip joints and a reduced accuracy in conformation of the socket and the caput than that of the above-mentioned metal-on-metal type artificial hip joint.

In addition to these drawbacks, all the above-described prior art artificial hip joints can not show an adhesion property to the human bone. In particular, for the prior art ceramic-to-ceramic type total artificial hip joint, in order to avoid problems caused due to insufficient strength of the resulting hip joint, it is necessary to remarkably increase a thickness of the socket, in the other words, it is essential to reduce the diameter of the caput in conformity to the increase of the thickness of the socket.

SUMMARY OF THE INVENTION

In view of the drawbacks of the artificial sockets of the prior art, the present invention has an object to provide an artificial socket which enables reduction of the thickness thereof to a lower level, in comparison with the prior art artificial sockets, without deteriorating the strength of the resulting socket. This enables an increase of the diameter of the central hollow portion thereof, that is, diameter of the artificial caput to be used in combination with the artificial socket.

Furthermore, the present invention also includes amongst its objects the provision of an artificial socket which has an excellent biocompatibility, does not deteriorate with time, is able to form fine bone-setting or ossificating lines or fibers, shows good water retention, and can inhibit adverse effects to human bone such as atrophy and dissolution of the bone due to powders of the worn socket.

Furthermore, the present invention has yet another object to provide an artificial hip joint using the artificial socket of the present invention, and a fixing screw suitable for securing the artificial socket in a pelvis of the human bone.

In one aspect thereof, the present invention provides an artificial socket comprising a composite of calcium phosphate compound and in vivo-absorptive polymeric material.

In another aspect thereof, the present invention provides a fixing screw for securing an artificial socket in a pelvis, which comprises a composite of calcium phosphate compound and in vivo-absorptive polymeric material.

In yet another aspect thereof, the present invention provides an artificial hip joint which comprises an artificial socket to be embedded and secured in a pelvis, and a stem which is embedded and secured in an upper end of the femur and a tip portion of which stem is provided with an artificial caput capable of being freely rotatably fitted in the artificial socket, in which the artificial socket comprises a composite of calcium phosphate compound and in vivo-absorptive polymeric material.

The present disclosure relates to subject matter contained in Japanese Patent Application No.09-000415 (filed on Jan. 6, 1997) which is expressly incorporated herein by reference in its entirety.

BRIEF DESCRIPTION OF THE DRAWINGS

The present invention will be more clearly understood from the description as set forth below with reference to the accompanying drawings, wherein:

FIG. 5 is a plan view illustrating another preferred embodiment of the artificial socket according to the present invention;

FIG. 6 is a cross-sectional view of the artificial socket of FIG. 5 taken along line VI—VI thereof;

FIG. 7 is a perspective view of the artificial socket of FIG. 5;

FIG. 8 is a plan view illustrating still another preferred embodiment of the artificial socket according to the present invention;

FIG. 9 is a cross-sectional view of the artificial socket of FIG. 8 taken along line IX—IX thereof; and FIG. 10 is a perspective view of the the artificial socket of FIG. 8.

DESCRIPTION OF THE PREFERRED EMBODIMENTS

Figure 1:
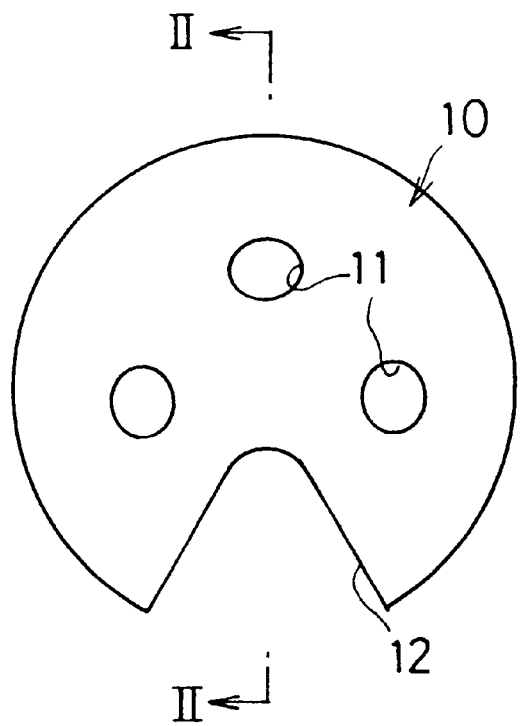
FIG. 1 is a plan view illustrating one preferred embodiment of the artificial socket according to the present invention.

The artificial socket and the fixing screw therefor according to the present invention is characterized by a composite which comprises calcium phosphate compound and in vivo-absorptive polymeric material.

The in vivo-absorptive polymeric material used herein includes, for example, a polylactic acid, a polyglycolic acid, a mixture of polylactic acid and polyglycolic acid, and a copolymer of lactic acid and glycolic acid. These polymeric materials may be used alone or in combination.

The in vivo-absorptive polymeric material, at an initial stage of embedding the artificial socket in a human bone, can exhibit a shock-absorbing function due to its elasticity, and, as a result of the replacement of the polymeric material with a living bone, the artificial socket can be integrally bonded to the pelvis. Using this polymeric material in the artificial socket, it becomes possible to increase the diameter of the central hollow portion of the artificial socket in the form of a semi-spherical shell body (i.e., according to the diameter of the artificial caput) to a level which is substantially the same as that of the human bone. As a result, a risk of subluxation of the hip joint can be diminished, and, because a high density polyethylene (HDP) is not used in the artificial socket, a risk of loosening of the stem positioned in the femur side of the human bone can be also diminished.

In addition, since the fixing screw is made from the same material as that of the artificial socket, as a whole and as a result of the combined function of the socket and the screw, it becomes possible to obtain a more preferable biocompatibility.

The calcium phosphate compound used herein includes, for example, hydroxyapatite, fluoroapatite, tricalcium phosphate, tetracalcium phosphate and calcium hydrogenphosphate. These calcium phosphate compounds may be used alone or in combination.

In the practice of the present invention, it is preferred that the in vivo-absorptive polymeric material is contained in an amount of about 5% to 80% in volume based on the calcium phosphate compound in the artificial socket. A content of the polymeric material of less than 5% in volume does not ensure a large effect and function as an elastic body of the polymeric material, and causes difficulty in the formation of the composite with the calcium phosphate compound. A content above 80% in volume causes difficulty in retaining the shape and condition of the artificial socket, after the in vivo-absorptive polymeric material has been absorbed in the living body (i.e., the pelvis). Furthermore, a hardness of the resulting artificial socket can be controlled by varifying a mixing ratio of the calcium phosphate compound and the polymeric material, and accordingly an artificial socket having the same hardness as that of the surface of a socket of a human bone can be obtained. The hardness and density of the composite is determined according to the ratio of the amount of calcium phosphate compound and the in vivo-absorptive polymeric material.

The artificial socket of the present invention is constituted from a semi-spherical shell body having a bored insertion through-hole for a fixing screw. In the artificial socket, in order to improve the fixing property of the socket in the pelvis, the outer side of the insertion through-holes may contain tubular bodies protruding from the outer surface of the semi-spherical shell body. The tubular bodies can be integrally bonded with the shell body via the insertion through-holes in a one-piece construction. Further, in order to assist in the early absorption of the polymeric material in the living body (i.e., the pelvis), the semi-spherical shell body, or both the semi-spherical shell body and the tubular bodies, may be constituted so that they have a meshed structure with a plurality of openings.

The artificial socket of the present invention may have an inner diameter of about 35 mm to 50 mm and a thickness of about 0.5 mm to 7.5 mm with regard to its semi-spherical shell body. A thickness of less than 0.5 mm indicates an insufficient strength, and a thickness above 7.5 mm causes difficulty in obtaining a largely increased diameter of the semi-spherical shell body.

In addition to the artificial socket and the inserting screw for the artificial socket, the present invention also pertains to an artificial hip joint. The hip joint according to the present invention comprises an artificial socket to be embedded and secured in a pelvis, and a stem which is embedded and secured in an upper end of the femur and a tip portion of the stem is provided with an artificial caput capable of being freely rotatably fitted in the artificial socket, and is characterized by the artificial socket comprising a composite of calcium phosphate compound and in vivo-absorptive polymeric material. The artificial socket used in the artificial hip joint of the present invention has been described in detail in the above paragraphs, and the production thereof will be described hereinafter.

In the artificial hip joint of the present invention, it is preferred that the inner diameter of the artificial socket and the outer diameter of the artificial caput of the stem each is in the range of about 35 mm to 50 mm.

The artificial socket of the present invention can be produced by fabricating a composite of a calcium phosphate compound and the in vivo-absorptive polymeric material to a predetermined configuration of the socket. In particular, using the hydroxyapatite and the polylactic acid as starting materials, the artificial socket of the present invention can be produced in accordance with, for example, the following method:

First, a slurry of hydroxyapatite is prepared from a phosphate compound and a calcium salt compound as the raw materials in accordance with conventional wet production methods. The resulting slurry is then dried in a rotary drum-type dryer to obtain powders of hydroxyapatite, and, after completion of the wet process, these powders are pulverized and calcined at a temperature of about 1200° C. to obtain particulates of hydroxyapatite having a particle size of about 100 $\mu$m to 300 $\mu$m. The resulting particulates are mixed with powdered polylactic acid, and the mixture is injected into a mold of the artificial socket to be produced, in accordance with conventional injection molding methods. An artificial socket having a predetermined configuration is thus obtained as a result of the injection molding process.

Alternatively, the artificial socket can be produced by using any other conventional method such as cast molding; turning (using a lathe), in which the press-molded powders of the calcium phosphate compound and the in vivo-absorptive polymeric material are fabricated on the lathe to obtain an artificial socket having the predetermined configuration, and the like.

According to the present invention, it becomes possible to obtain a thin and elastic artificial socket, and also to bond a ceramic caput or head to the stem of the femur. The artificial hip joint of the present invention is classified under the group of the above-described ceramic-to-ceramic type of total artificial hip joint. However, it can be clearly distinguished from the conventional ceramic-to-ceramic type of total artificial hip joints in which alumina or zirconia is used as the ceramic material. That is, the conventional hip joints ensure a hard-to-hard connection of the joint, whereas the hip joint of the present invention ensures a soft-to-hard connection of the joint, thereby enabling to obtain a good shock absorption which can not be obtained in the conventional hard-to-hard artificial hip joints.

Furthermore, according to the present invention, compatibility and water retention in the adjacent joint surfaces can be improved, and accordingly, a good lubricating property can be obtained. As a result, durability or resistance to abrasion can be remarkably improved, and thus, adverse effects to the bone such as atrophy and dissolution of the bone due to powders of the worn socket can be prevented.

Furthermore, since the obtained artificial socket exhibits a good lubricating property and has a thin body, it enables the use, in combination with the socket, of a large-sized caput, thereby ensuring the provision of a stable hip joint which can be moved within a wide range of movement without causing dislocation of the joint.

EXAMPLES

The present invention will be further described with regard to some preferred examples of the artificial socket, fixing screw and artificial hip joint of the present invention referring to the accompanying drawings. Note, however, that the present invention should not be restricted to these examples.

Figure 2:
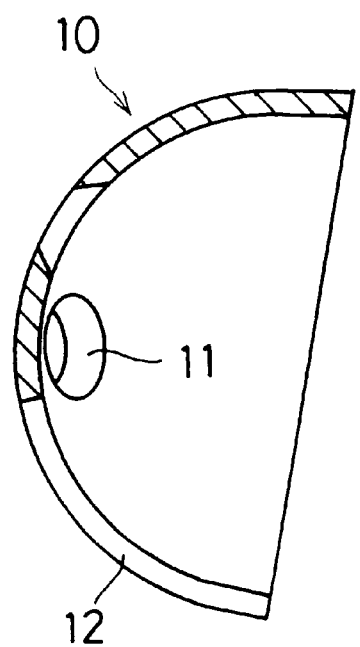
FIG. 2 is a cross-sectional view of the artificial socket of FIG. 1 taken along line II—II thereof.
Figure 3:
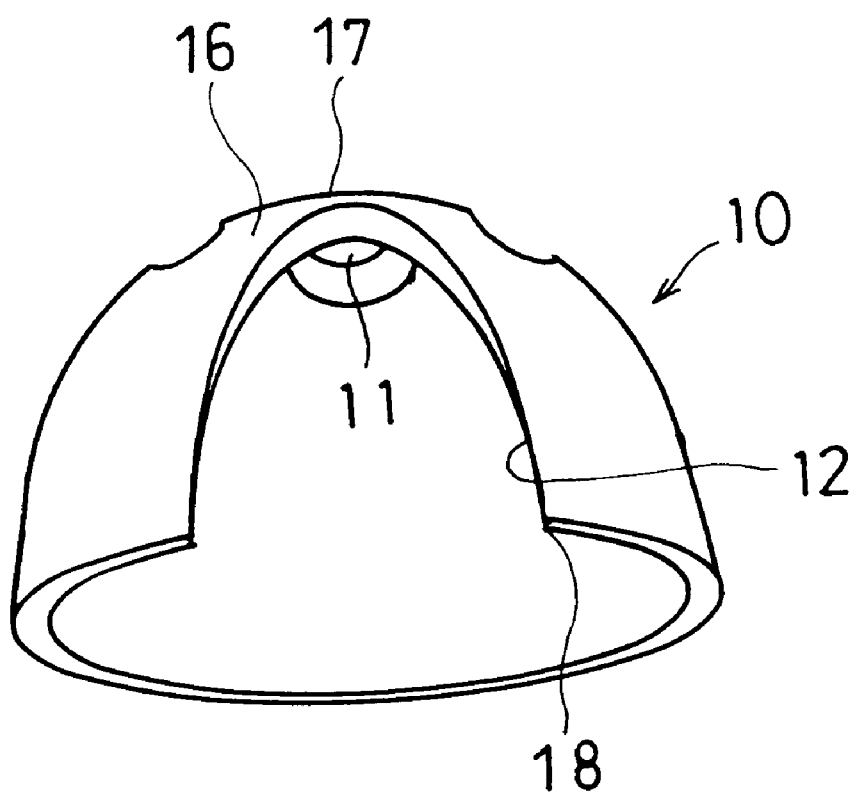
FIG. 3 is a perspective view of the artificial socket of FIG. 1.

FIGS. 1 to 3 illustrate the artificial socket according to one preferred embodiment of the present invention. The artificial socket is constituted from a semi-spherical shell body 10, and includes at a ceiling part 16, i.e., an upper part of the shell body 10, three insertion through-holes 11 for a fixing screw, each of which is bored at a substantially equivalent distance from the ceiling part 16, and equally spaced from each other. Further, as is illustrated, the artificial socket has a notched space 12, ranging from an open-ended surface 18 thereof to the ceiling part 16. The notched space 12 can be produced in any manner such as the socket being molded to the notched space 12 by removing a part of the shell body 10 in conformity with the configuration of the socket of the living body (i.e, the pelvis).

While the illustrated embodiments include three through-holes, it is noted that any number of through holes can be incorporated in the artificial socket, including one or two through-holes.

Figure 4:
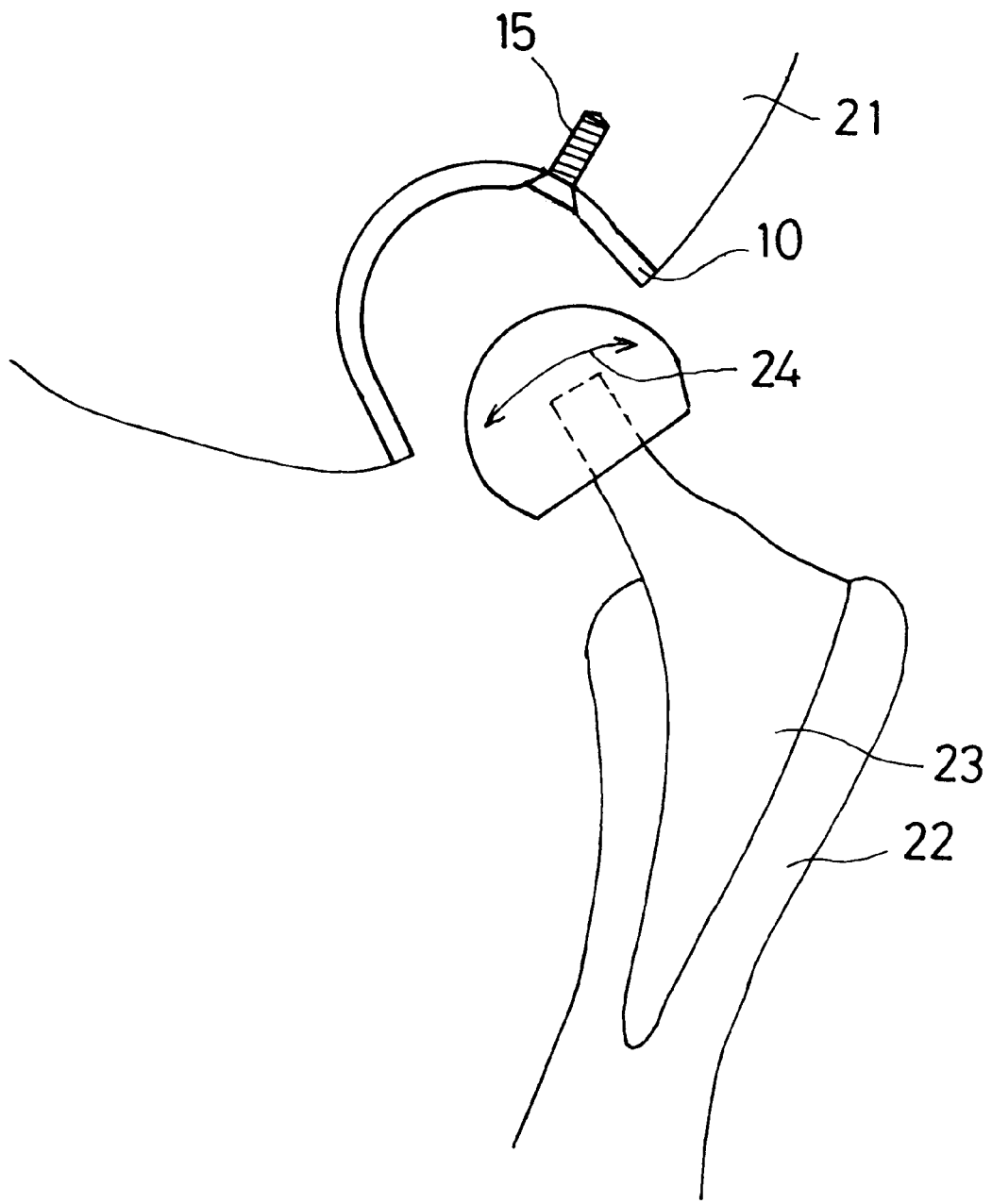
FIG. 4 is a simplified cross-sectional view illustrating embedding of the artificial hip joint according to one preferred embodiment of the present invention in a human bone.

The artificial socket, as is illustrated in FIG. 4, is embedded in and secured to a predetermined site of the pelvis 21. Securing of the artificial socket can be carried out by using a fixing screw 15 which is designed to be inserted into and passed through the insertion through-holes 11 of the semi-spherical shell body 10, followed by being screwed into the pelvis 21. On the femur 22, a stem 23 is embedded and secured to an upper end thereof. Further, a semi-spherical artificial caput 24 is fixedly mounted on a tip of the stem 23. The artificial caput 24 is designed so that it is inserted into the artificial socket, and the inserted caput 24 can be freely rotated and moved within a concave surface of the semi-spherical artificial socket.

In the illustrated embodiment, the semi-spherical shell body 10 constituting the artificial socket and the inserting screw 15 are produced from the same material containing a calcium phosphate compound and an in vivo-absorptive polymeric material. Further, the stem 23 is produced from an alloy such as titanium alloy, Co—Cr alloy and the like, and the artificial caput 24 is produced from ceramics such as alumina (Al2O3) and the like, or an alloy such as Co—Cr alloy and the like.

An inner diameter of the semi-spherical shell body 10 of the artificial socket and an outer diameter of the artificial caput 24 each is in the range of about 35 mm to 50 mm.

Production Example

The following is one example describing the production of the artificial socket and inserting screw for the socket according to the present invention. Hydroxyapatite and polylactic acid are employed as starting materials.

A slurry of hydroxyapatite was produced in the conventional wet process. The slurry of hydroxyapatite was dried on a spray dryer to obtain hydroxyapatite powders. After wet molding, the powders were pulverized and calcined at a temperature of 1200° C. to obtain hydroxyapatite particles having a particle size of 100 $\mu$m to 300 $\mu$m. The hydroxyapatite particles and the powdered polylactic acid were mixed in a ratio (volume) of 70:30, and the mixture was injection molded in a mold at a temperature of 1200° C. on an injection molding machine. A large artificial socket having a configuration similar to that of the artificial socket illustrated in FIGS. 1 to 3 was thus produced. A fixing screw for securing the artificial socket was produced according to the same injection molding method as above.

FIGS. 5 to 7 illustrate the artificial socket according to another preferred embodiment of the present invention. The artificial socket is similar to that of the embodiment illustrated in FIGS. 1 to 3, however, in the illustrated embodiment, each of the insertion through-holes 11 have a tubular projection 13 protruding from an outer side thereof. The tubular projection 13 is integrally bonded to the semi-spherical shell body 10 via the insertion through-holes 11 in a one-piece construction. Using this artificial socket, it is expected that the socket-to-pelvis fixing and securing properties can be improved. Though each of the through-holes 11 including a tubular projection is illustrated, any number of the through-holes can include a tubular projection.

FIGS. 8 to 10 illustrate the artificial socket according to yet another preferred embodiment of the present invention. The artificial socket is similar to that of the embodiment illustrated in FIGS. 5 to 7, however, in the illustrated embodiment, a plurality of openings 14 were bored in each of the semi-spherical shell body 10 and the tubular projection 13 to obtain a meshed structure therein. Using this artificial socket, it is expected that the in vivo-absorptive polymeric material of the socket will be absorbed at an early stage into a living body (i.e., the pelvis), after the socket is embedded in the pelvis.

Alternatively, the openings 14 may be bored only in the semi-spherical shell body 10. Of course, in the above embodiment described referring to FIGS. 1 to 3, a plurality of openings 14 may be bored in the semi-spherical shell body 10 to obtain a meshed structure. Moreover, the openings 14 can be on only a portion of the shell body and/or the tubular projections or can cover the entire shell body and/or the tubular projections.

As can be appreciated from the detailed descriptions of the present invention in the above paragraphs, according to the present invention, there can be provided an artificial socket and inserting screw for the socket having excellent biocompatibility and strength; since they are constituted from a composite which comprises a calcium phosphate compound having an excellent biocompatibility with bone, and an in vivo-absorptive polymeric material capable of exhibiting excellent elasticity properties in the initial stage of embedding of the socket and screw and also capable of being replaced with the bone. Therefore, the thickness of the artificial socket can be notably reduced in comparison with the conventional artificial sockets, and thus an inner diameter of the semi-spherical shell body constituting the socket can be increased to a level which is substantially equivalent to the diameter of the real sockets in the living body (i.e., the pelvis). As a result, a risk of subluxation can be diminished in the artificial hip joint using such an artificial socket. Also, a risk of loosening of the stem can be diminished, because no polyethylene is used in the artificial socket and accordingly powders of the worn socket (cause of said loosening) are not produced.

Further, according to the present invention, there is provided an artificial hip joint in which the polymeric material contained is absorbed in a living body (i.e., the pelvis) with time, and then, as a function of the bone induction property of the calcium phosphate compound contained, fine bone-setting lines which are integral with the calcium phosphate compound are formed on the surface of the bone tissue of the artificial socket.

Furthermore, since said polymeric material has good water retention properties and therefore its wear due to increase of the friction coefficient with the caput can be diminished to a minimum, there can be provided an artificial socket which does not cause any adverse effects to the bone such as atrophy and dissolution of the bone due to powders of the worn socket.

Although the invention has been described with reference to particular means, materials and embodiments, it is to be understood that the invention is not limited to the particulars disclosed and extends to all equivalents within the scope of the claims.

We claim:

1. An artificial socket comprising a composite of calcium phosphate compound and in vivo-absorptive polymeric material, said composite being structured and arranged in a form including a hollow portion configured to receive a caput.

2. The artificial socket according to claim 1, wherein said form comprises a semi-spherical shell body.

3. The artificial socket according to claim 2, wherein said in vivo-absorptive material is at least one member selected from the group consisting of polylactic acid, polyglycolic acid, a mixture of polylactic acid and polyglycolic acid, and a copolymer of lactic acid and glycolic acid.

4. The artificial socket according to claim 3, wherein said calcium phosphate compound is at least one member selected from the group consisting of hydroxyapatite, fluoroapatite, tricalcium phosphate, tetracalcium phosphate and calcium hydrogenphosphate.

5. The artificial socket according to claim 4, wherein said in vivo-absorptive polymeric material is contained in an amount of about 5% to 80% by volume based on said calcium phosphate material.

6. The artificial socket according to claim 4, wherein said semi-spherical shell body has an inner diameter of about 35 mm to 50 mm and a thickness of about 0.5 mm to 7.5 mm.

7. The artificial socket according to claim 5, wherein said semi-spherical shell body has an inner diameter of about 35 mm to 50 mm and a thickness of about 0.5 mm to 7.5 mm.

8. The artificial socket according to claim 2, wherein said semi-spherical shell body includes at least one bore insertion through-hole for a fixing screw.

9. The artificial socket according to claim 8, wherein said semi-spherical shell body includes a mesh structure with a plurality of openings.

10. The artificial socket according to claim 9, further including a tubular body protruding from an outer surface of said semi-spherical shell body, said tubular body communicating with said insertion through-hole.

11. The artificial socket according to claim 10, wherein said semi-spherical shell body and said tubular body both have a meshed structure with a plurality of openings.

12. The artificial socket according to claim 8, further including a tubular body protruding from an outer surface of said semi-spherical shell body, said tubular body communicating with said insertion through-hole.

13. The artificial socket according to claim 12, wherein said semi-spherical shell body and said tubular body both have a meshed structure with a plurality of openings.

14. The artificial socket according to claim 3, wherein said semi-spherical shell body has an inner diameter of about 35 mm to 50 mm and a thickness of about 0.5 mm to 7.5 mm.

15. The artificial socket according to claim 1, wherein said in vivo-absorptive material is at least one member selected from the group consisting of polylactic acid, polyglycolic acid, a mixture of polylactic acid and polyglycolic acid, and a copolymer of lactic acid and glycolic acid.

16. The artificial socket according to claim 15, wherein said calcium phosphate compound is at least one member selected from the group consisting of hydroxyapatite, fluoroapatite, tricalcium phosphate, tetracalcium phosphate and calcium hydrogenphosphate.

17. The artificial socket according to claim 16, wherein said in vivo-absorptive polymeric material is contained in an amount of about 5% to 80% by volume based on said calcium phosphate material.

18. The artificial socket according to claim 1, wherein said calcium phosphate compound is at least one member selected from the group consisting of hydroxyapatite, fluoroapatite, tricalcium phosphate, tetracalcium phosphate and calcium hydrogenphosphate.

19. The artificial socket according to claim 1, wherein said in vivo-absorptive polymeric material is contained in an amount of about 5% to 80% by volume based on said calcium phosphate material.

20. The artificial socket according to claim 1, wherein said hollow portion has an inner diameter of about 35 mm to 50 mm and a thickness of about 0.5 mm to 7.5 mm.

21. In combination, an artificial socket as recited in claim 1, and a fixing screw, said fixing screw comprising a composite of calcium phosphate compound and in vivo-absorptive polymeric material.

22. A artificial hip joint, comprising:

an artificial socket to be embedded and secured in a pelvis;

a stem which is to be embedded and secured in an upper end of the femur, said stem including a tip portion including an artificial caput capable of being freely rotatably fitted in said artificial socket; and said artificial socket comprising a composite of calcium phosphate compound and in vivo-absorptive polymeric material, said composite being structured and arranged in a form including a hollow portion configured to receive said caput.

23. The artificial hip joint according to claim 22, wherein said form comprises a semi-spherical shell body.

24. The artificial hip joint according to claim 23, wherein an inner diameter of said semi-spherical shell body and an outer diameter of said artificial caput each is in a range of about 35 mm to 50 mm.

25. The artificial hip joint according to claim 24, wherein said semi-spherical shell body has a thickness of about 0.5 mm to 7.5 mm.

* * * * *